United States Patent
Xu et al.

(10) Patent No.: US 11,020,367 B2
(45) Date of Patent: Jun. 1, 2021

(54) METHOD FOR PREPARING MEDICINE WITH DICAFFEOYLQUINIC ACID FOR TREATING GOUT

(71) Applicant: Huazhong Agricultural University, Wuhan (CN)

(72) Inventors: Xiaoyun Xu, Wuhan (CN); Ting Wu, Wuhan (CN); Weiwei Cao, Wuhan (CN); Siyi Pan, Wuhan (CN); Hui Li, Wuhan (CN)

(73) Assignee: Huazhong Agricultural University, Wuhan (CN)

( * ) Notice: Subject to any disclaimer, the term of this patent is extended or adjusted under 35 U.S.C. 154(b) by 0 days.

(21) Appl. No.: 16/566,886

(22) Filed: Sep. 11, 2019

(65) Prior Publication Data

US 2020/0000761 A1 Jan. 2, 2020

(30) Foreign Application Priority Data

Jun. 10, 2019 (CN) .......................... 201910496409.X

(51) Int. Cl.
*A61K 31/216* (2006.01)

(52) U.S. Cl.
CPC ...... *A61K 31/216* (2013.01); *A61K 2236/333* (2013.01)

(58) Field of Classification Search
CPC . A61K 31/216; A61K 2236/333; A61P 19/06; C07C 67/48; C07C 2601/14
See application file for complete search history.

(56) References Cited

PUBLICATIONS

Yan Jiang et al., Caffeoylquinic acid derivatives rich extract from Gnaphalium pensylvanicum willd. Ameliorates hyperuricemia and acute gouty arthritis in animal model, BMC Complementary and Alternative Medicine (2017) 17:320, DOI 10.1186/s12906-017-1834-9 (Year: 2017).*

* cited by examiner

*Primary Examiner* — Sarah Pihonak
*Assistant Examiner* — Jason Deck

(57) ABSTRACT

1,4-dicaffeoylquinic acid is used as a xanthine oxidase inhibitor and in preparation of a medicament for treating gout. The present invention is the first to isolate and identify a dicaffeoylquinic acid compound from *Artemisia selengensis* leaves. The compound not only has an ability of inhibiting xanthine oxidase activity, but also has the function of anti-gout inflammation, which can be better used for treating gout. The dicaffeoylquinic acid is derived from natural plants and has the advantages of being safe and non-toxic, and having fewer side effects.

1 Claim, 1 Drawing Sheet

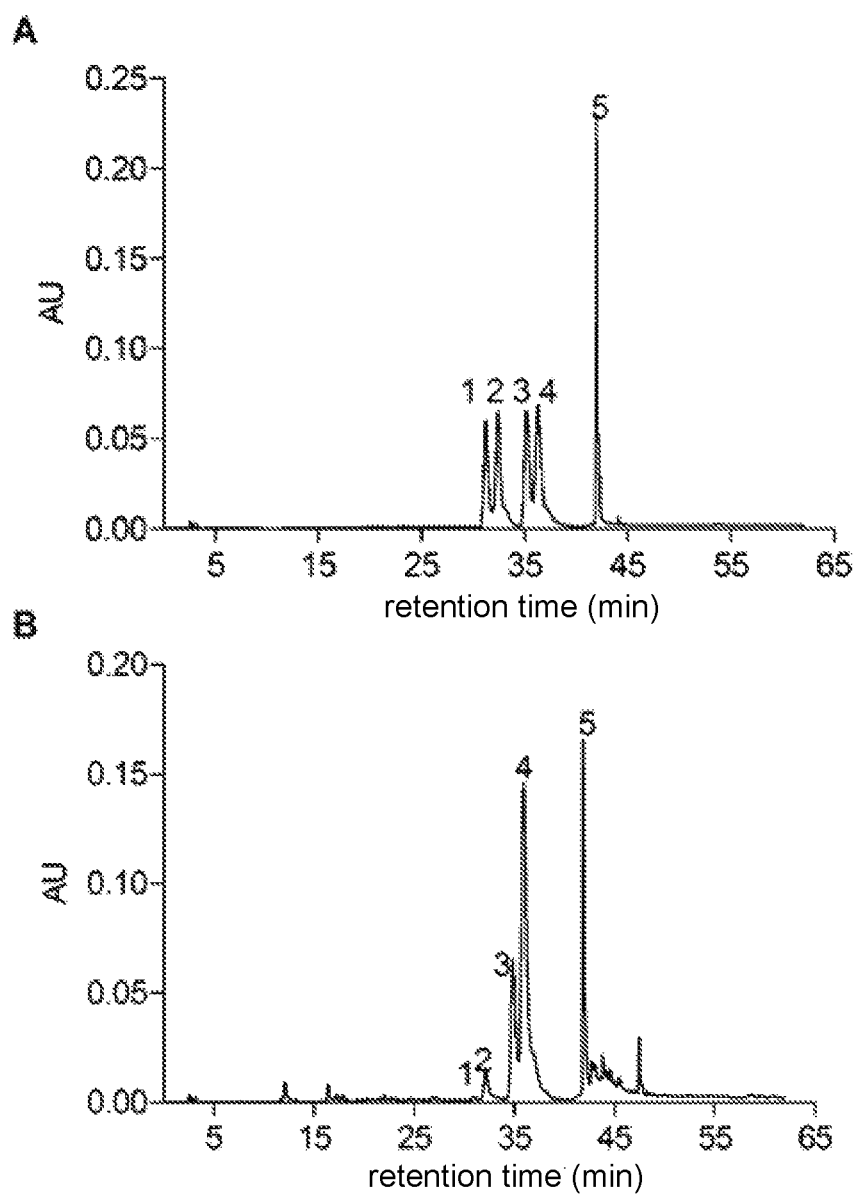

METHOD FOR PREPARING MEDICINE WITH DICAFFEOYLQUINIC ACID FOR TREATING GOUT

CROSS REFERENCE OF RELATED APPLICATION

The present invention claims priority under 35 U.S.C. 119(a-d) to CN 201910496409.X, filed Jun. 10, 2019.

BACKGROUND OF THE PRESENT INVENTION

Field of Invention

The present invention relates to a pharmaceutical use of dicaffeoylquinic acid, and more particularly to a method for preparing a medicine for treating hyperuricemia and gout, and belongs to a field of botanical medicine.

Description of Related Arts

Gout is a disease in which uric acid is deposited in tissues due to an increase in blood uric acid or a decrease in renal excretion of uric acid caused by a disorder of sputum metabolism. Hyperuricemia is the biochemical basis of gout, and gout has become a common disease that threatens human health such as hypertension, diabetes, and atherosclerosis. Xanthine oxidase (XOD) is a key enzyme in the metabolism of sputum. It can catalyze the production of uric acid from jaundice and hypoxanthine. The increase of XOD activity will cause an increase in uric acid level, leading to hyperuricemia. When too much uric acid in the body is deposited in the form of crystals in the synovial membrane and interstitial fluid of the joint, it will cause a series of inflammatory reactions and cause gouty arthritis. Therefore, inhibition of xanthine oxidase can prevent hyperuricemia, reduce the production of uric acid, and thus prevent the occurrence of gout inflammation. Conventionally, western medicine for treating hyperuricemia and gout has great side effects such as gastrointestinal discomfort and liver and kidney damage, and some natural products such as polyphenols, flavonoids, and triterpenes have the advantages of multiple targets and low toxic side effects in the treatment of gout.

*Artemisia selengensis* leaves are rich in a variety of active ingredients such as flavonoids, polyphenols and other compounds. It has been reported that caffeoylquinic acid in the leaves of *Artemisia selengensis* can inhibit the activity of XOD, but polyphenols as secondary metabolites of plants have wide varieties. Factors such as climate and geographic location also affect the varieties of secondary metabolites of plants. Therefore, it is necessary to excavate more natural products that inhibit xanthine oxidase and relieve gout inflammation from the vegetable processing by-product of *Artemisia selengensis* leaves.

SUMMARY OF THE PRESENT INVENTION

Since conventional drugs for treating hyperuricemia and gout inflammation have many side effects, an object of the present invention is to provide a dicaffeoylquinic acid compound derived from *Artemisia selengensis* leaves as a xanthine oxidase inhibitor and a method for preparing a medicine for treating gout by using the same.

The object of the present invention is achieved by the following technical solutions.

First, *Artemisia selengensis* leaves are extracted with 50% ethanol, petroleum ether, and ethyl acetate to obtain the ethyl acetate fraction of the *Artemisia selengensis* leaves. The ethyl acetate fraction is then subjected to high performance liquid chromatography quadrupole time-of-flight mass spectrometry (HPLC-Q/TOF-MS) to identify five dicaffeoylquinic acid compounds in the ethyl acetate fraction. Finally, $IC_{50}$ values of the above-mentioned dicaffeoylquinic acid compound in inhibiting xanthine oxidase are determined by an enzyme kinetic method, and a gout inflammation model is established by using THP-1 cells stimulated by lipopolysaccharide and sodium urate, so as to determine effects of the above five kinds of dicaffeoylquinic acid compounds on gout inflammation.

Results shows that the five dicaffeoylquinic acid compounds isolated from the *Artemisia selengensis* leaves are 1,4-dicaffeoylquinic acid, 3,4-dicaffeoylquinic acid, 1,5-dicaffeoylquinic acid, 3,5-dicaffeoylquinic acid and 4,5-dicaffeoylquinic acid, all of which have certain inhibition of xanthine oxidase activity, indicating uric acid lowering function and potential for treating hyperuricemia, wherein 1,4-dicaffeoylquinic acid is first reported in the *Artemisia selengensis* leaves, and ability thereof for inhibiting the xanthine oxidase activity is significantly higher than those of the other four compounds.

At the same time, the five kinds of the dicaffeoylquinic acid, except the 3,5-dicaffeoylquinic acid, can all inhibit increase of IL-1β secretion level of THP-1 cells induced by lipopolysaccharide and sodium urate. IL-1β secretion inhibiting functions of 1,4-dicaffeoylquinic acid and 1,5-dicaffeoylquinic acid are better than those of other dicaffeoylquinic acids, indicating anti-gout inflammation functions and potential to alleviate clinical symptoms of gouty arthritis.

Using 1,4-dicaffeoylquinic acid for treating gout can reduce the production of uric acid from the source as well as effectively alleviate the symptoms of inflammation, and has better curative effect and application value.

The present invention has advantages as follows.

The present invention is the first to isolate and identify a dicaffeoylquinic acid compound, 1,4-dicaffeoylquinic acid, from *Artemisia selengensis* leaves. The compound not only has a significant ability of inhibiting xanthine oxidase activity, but also has the function of anti-gout inflammation, which can be better used for treating gout.

The present invention combines a leaching method with liquid-liquid extraction, and uses a semi-preparative high-performance liquid chromatography to separate the chemical components in the *Artemisia selengensis* leaves. Compared with chemical synthesis methods, the present invention has the advantages of simple operation, low cost and high efficiency.

The dicaffeoylquinic acid of the present invention is derived from natural plants and has the advantages of being safe and non-toxic, and having fewer side effects.

BRIEF DESCRIPTION OF THE DRAWINGS

FIGURE is a liquid chromatogram of an ethyl acetate fraction of *Artemisia selengensis* leaves and five mixed standards; wherein A: mixed standards, B: ethyl acetate fraction of *Artemisia selengensis* leaves.

DETAILED DESCRIPTION OF THE PREFERRED EMBODIMENT

Embodiment 1: Extraction and Identification of Dicaffeoylquinic Acid

*Artemisia selengensis* leaves were dried in an oven at 60° C. for 20 h, and pulverized through a 60-mesh sieve to obtain powder of the *Artemisia selengensis* leaves.

The powder of the *Artemisia selengensis* leaves was extracted with 50% (by volume) ethanol, and a ratio of material to liquid was 1:15. The mixture was stirred for 1 hour at room temperature, extracted twice and filtered wherein the filtrate was combined. After removing ethanol by rotary evaporation, a concrete of the *Artemisia selengensis* leaves was obtained.

The concrete was extracted with petroleum ether and ethyl acetate in sequence to obtain an extract of the *Artemisia selengensis* leaves. The ethyl acetate extract layer was rotary evaporated to remove ethyl acetate, and lyophilized to obtain powder of the ethyl acetate fraction of the *Artemisia selengensis* leaves.

The ethyl acetate fraction of the above-mentioned *Artemisia selengensis* leaves was placed in a 5 mg/mL methanol solution. An Agilent HPLC-Q/TOF-MS was used to identify monomer composition which was compared to standards. Mobile phases were A: 0.1% formic acid and B: acetonitrile. Gradient elution conditions were: 0-10 min, 10% B; 10-15 min, 15% B; 15-17 min, 18% B; 17-37 min, 18% B; 37-42 min, 50% B; 42-48 min, 65% B; 48-52 min, 80% B; 52-58 min, 80% B; 58-62 min, 10%, B. Mass spectrometry conditions were: ESI source, negative ion mode to acquisition signal, scan range 100-1100 m/z, capillary voltage, 3.5 kV; nebulizer gas pressure, 50 psi; dry gas flow rate, 10.0 L/min; desolvation temperature, 325° C. Fragator voltage was: 175 V. Collision energy was: 10-40 V.

It can be seen from FIGURE that the retention times of the five peaks of the ethyl acetate fraction of the *Artemisia selengensis* leaves are the same as the retention times of the mixed standards, respectively, which are 1,4-dicaffeoylquinic acid (1,4-diCQA), 3,4-dicaffeoylquinic acid (3,4-diCQA), 1,5-dicaffeoylquinic acid (1,5-diCQA), 3,5-dicaffeoylquinic acid (3, 5-diCQA), and 4,5-dicaffeoylquinic acid (4,5-diCQA).

It can be seen from Table 1 that mass spectrometry fragment information of the five peaks of the ethyl acetate fraction of the *Artemisia selengensis* leaves meets fragment information of the five standards, and the retention times are the same as shown in FIGURE, which proves that the *Artemisia selengensis* leaves contain these five compounds, wherein a content of the 1,4-dicaffeoylquinic acid in the ethyl acetate fraction of the *Artemisia selengensis* leaves is 0.39%. The 1,4-dicaffeoylquinic acid has not been reported in the *Artemisia selengensis* leaves, and the present invention is the first to report that the 1,4-dicaffeoylquinic acid is present in the *Artemisia selengensis* leaves.

TABLE 1

HPLC-Q/TOF-MS identification of chemical constituents in ethyl acetate fraction of Artemisia selengensis leaves

| Peak | RT (t/min) | $[M - H]^-$ m/z | $MS^2$ m/z (% base peak) | Molecular formula | compounds | Content (g/100 gdw) |
|---|---|---|---|---|---|---|
| 1 | 31.029 | 515.1198 | 353 (100), 299 (26.7), 203 (49.0) | $C_{25}H_{24}O_{12}$ | 1,4-diCQA | 0.39 ± 0.09 |
| 2 | 32.162 | 515.1162 | 353 (100), 335 (20.3), 179 (72.0) | $C_{25}H_{24}O_{12}$ | 3,4-diCQA | 1.39 ± 0.07 |
| 3 | 34.876 | 515.1197 | 353 (100), 191 (44.9), 179 (6.1), | $C_{25}H_{24}O_{12}$ | 1,5-diCQA | 6.85 ± 0.26 |
| 4 | 35.949 | 515.1208 | 353 (100), 191 (16.8), 179 (9.4) | $C_{25}H_{24}O_{12}$ | 3,5-diCQA | 13.06 ± 0.54 |
| 5 | 41.900 | 515.1100 | 353 (100), 191 (18.6), 179 (51.6) | $C_{25}H_{24}O_{12}$ | 4,5-diCQA | 4.72 ± 0.17 |

Embodiment 2: Inhibition of XOD Enzyme Activity by Dicaffeoylquinic Acid

Twenty μL of the above identified five monomeric compound solutions from the *Artemisia selengensis* leaves and positive control (allopurinol) were pipetted into enzyme labels before adding 100 μL of XOD enzyme solution (0.02 U/mL), and vibrating in a 37° C. microplate reader for 10 s to incubate for 2 min. Forty μL of xanthine solution (1 mmol/L) was added with a spray gun to measure absorbance every 20 s for 15 times. Change of absorbance in the reaction system at 295 nm within 5 min was $K_1$, and the change in PBS control was $K_0$.

The inhibition rate (%) of the samples on XOD enzyme activity=$(1-K_1/K_0) \times 100\%$.

As can be seen from Table 2, among the five compounds, 1,4-diCQA has the lowest $IC_5O$ value and is lower than that of the allopurinol (positive drug). This indicates that 1,4-diCQA in the *Artemisia selengensis* leaves has a good ability to inhibit XOD enzyme activity, and it can be applied to product development for preventing hyperuricemia.

TABLE 2

$IC_{50}$ of five monomeric compounds in ethyl acetate fraction of Artemisia selengensis leaves in inhibiting XOD

| | $IC_{50}/(\mu M)$ |
|---|---|
| 3,5-diCQA | 288.87 ± 21.78 |
| 3,4-diCQA | 260.23 ± 18.35 |
| 4,5-diCQA | 233.12 ± 10.90 |
| 1,4-diCQA | 7.36 ± 0.63 |
| 1,5-diCQA | 121.52 ± 2.56 |
| allopurinol (positive drug) | 12.15 ± 0.32 |

Embodiment 3: Effect of Dicaffeoylquinic Acid on Relieving Gout Inflammation

THP-1 suspension cells were inoculated into a 24-well plate. When the density reached 80%, a phorbol ester (PMA) solution with a final concentration of 100 ng/mL was added. After 12 hours of PMA treatment, THP-1 cells differentiated into adherent macrophages. Culture medium was aspirated before washing the cells with PBS, completely replacing the culture medium to culture for 12 h before carrying out a dosing treatment. One hundred μmol/L of the above identified monomer compounds were pre-incubated for 12 h, then lipopolysaccharide with a final concentration of 1 μg/mL was added and acted for 2 h, and finally a sodium urate solution with a final concentration of 200 μg/mL was added and acted for 4 h. The control group did not add drugs, and did not stimulate the cells with lipopolysaccharide and sodium urate. The model group was pre-incubated without drugs, and cells were stimulated with lipopolysaccharide and sodium urate. Finally, the cell supernatant was collected, centrifuged, and IL-1β content in the supernatant was measured by using an ELISA kit.

As can be seen from Table 3, lipopolysaccharide and sodium urate led to a significant increase in secretion level of IL-1β in the model group. Except 3,5-dicaffeoylquinic acid, the other four types of dicaffeoylquinic acid can all inhibit the increase in the level of IL-1β. There was no significant difference in the increase of IL-1β caused by 1,4-diCQA and 1,5-diCQA in inhibiting lipopolysaccharide and sodium urate, but their inhibition of IL-1β secretion was superior to those of other dicaffeoylquinic acid. It indicates that 1,4-diCQA can be applied to product development against gout inflammation.

TABLE 3

Effects of dicaffeoylquinic acid on secretion of IL-1β in THP-1 cells stimulated by lipopolysaccharide and sodium urate

|  | IL-1β (pg/mL) |
| --- | --- |
| Control group | $214.83 \pm 11.92^{a}$ |
| Model group | $8747.09 \pm 975.97^{e}$ |
| 3,5-diCQA | $8850.00 \pm 190.20^{e}$ |
| 3,4-diCQA | $7088.57 \pm 621.91^{d}$ |
| 4,5-diCQA | $5572.09 \pm 632.81^{c}$ |
| 1,4-diCQA | $4647.67 \pm 607.03^{bc}$ |
| 1,5-diCQA | $4176.74 \pm 1214.41^{b}$ |

From the results of the above embodiments, the present invention identifies a novel compound 1,4-dicaffeoylquinic acid in the *Artemisia selengensis* leaves by HPLC-Q/TOF-MS, which not only has a good inhibition of xanthine oxidase, but also can significantly inhibit the gout inflammation caused by sodium urate, which indicates that 1,4-dicaffeoylquinic acid of the *Artemisia selengensis* leaves can be developed into a product for preventing hyperuricemia and gout.

What is claimed is:

1. A method for preparing a medicine for treating gout, comprising steps of: extracting the *Artemisia selengensis* leaves with 50% ethanol, and concentrating into a concrete before further extracting with petroleum ether and ethyl acetate, and finally separating a 1,4-dicaffeoylquinic acid with a semi-preparative liquid chromatograph; then using the 1,4-dicaffeoylquinic acid as a xanthine oxidase inhibitor in the medicine.

* * * * *